(12) United States Patent
Zu et al.

(10) Patent No.: US 10,704,101 B2
(45) Date of Patent: Jul. 7, 2020

(54) METHOD FOR DETECTION OF A GENETIC VARIANT

(71) Applicant: Agency for Science, Technology and Research, Singapore (SG)

(72) Inventors: Yanbing Zu, Singapore (SG); Jackie Y. Ying, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 36 days.

(21) Appl. No.: 16/032,707

(22) Filed: Jul. 11, 2018

(65) Prior Publication Data
US 2019/0024175 A1    Jan. 24, 2019

Related U.S. Application Data

(62) Division of application No. 15/022,548, filed as application No. PCT/SG2014/000442 on Sep. 17, 2014, now Pat. No. 10,041,121.

(30) Foreign Application Priority Data

Sep. 17, 2013   (SG) .................................. 201307025

(51) Int. Cl.
 *C12Q 1/6883* (2018.01)
 *C12Q 1/6827* (2018.01)
 *C12Q 1/6881* (2018.01)
 *G01N 21/78* (2006.01)

(52) U.S. Cl.
 CPC ......... *C12Q 1/6883* (2013.01); *C12Q 1/6827* (2013.01); *C12Q 1/6881* (2013.01); *G01N 21/78* (2013.01); *C12Q 2600/106* (2013.01); *C12Q 2600/156* (2013.01); *C12Q 2600/158* (2013.01); *C12Q 2600/16* (2013.01)

(58) Field of Classification Search
 CPC .............................. C12Q 1/6863; G01N 21/78
 See application file for complete search history.

(56) References Cited

U.S. PATENT DOCUMENTS

2008/0085839 A1    4/2008 Klapproth
2008/0311561 A1 *  12/2008 Ahn ....................... C12Q 1/708
                                                                        435/5

FOREIGN PATENT DOCUMENTS

WO    2011087456 A1    7/2011
WO    2014168582 A1   10/2014

OTHER PUBLICATIONS

Zu et al., "Nanoprobe-Based Genetic Testing," Nano Today, vol. 9, 2014, pp. 166-171.
Holly Ahern, "Biochemical, Reagents Kits Offer Scientists Good Return on Investment," The Scientist, vol. 9, No. 15, Jul. 24, 1995, p. 20.
International Preliminary Report on Patentability for International Application No. PCT/SG2014/000442 dated Mar. 22, 2016, pp. 1-9.
Zu et al., "Visualizing Low-Level Point Mutations: Enzyme-like Selectivity Offered by Nanoparticle Probes," Small, vol. 7, No. 3, 2011, pp. 306-310.
Ruiter et al., "CYP2C19*2 Polymorphism is Associated with Increased Survival in Breast Cancer Patients Using Tamoxifen," Pharmacogenomics, vol. 11, No. 10, Oct. 2010, pp. 1367-1375, see Abstract.
Morel et al., "Clinical Relevance of Different Dihydropyrimidine Dehydrogenase Gene Single Nucleotide Polymorphisms on 5-Fluorouracil Tolerance," Molecular Cancer Therapeutics, vol. 5, No. 11, Nov. 2006, pp. 2895-2904.
Man et al. "Association Between HLA-B* 1502 Allele and Antiepileptic Drug-Induced Cutaneous Reactions in Han Chinese," Epilepsia, vol. 48, No. 5, 2007, pp. 1015-1018.
GenBank Accession No. AF261085.1, "*Homo sapiens* Glyceraldehyde-3-Phosphate Dehydrogenase (GADPH) mRNA, Complete cds," https://www.ncbi.nlm.nih.gov/nuccore/AF261085.1, sequence submitted Apr. 27, 2000, pp. 1-2.
Cheng et al., "New Testing Approach in HLA Genotyping Helps Overcome Barriers in Effective Clinical Practice," Clinical Chemistry, vol. 55, No. 8, 2009, pp. 1568-1572.

\* cited by examiner

*Primary Examiner* — Narayan K Bhat
(74) *Attorney, Agent, or Firm* — Winstead PC

(57) ABSTRACT

A method and kit for detecting a genetic variant associated with a disease or disorder, including incompatibility with a pharmaceutical. The method and kit using a first nanoparticle coupled to at least one morpholino nucleic acid probe comprising a target complimentary region base sequence that is a perfect match to a genetic variant sequence.

14 Claims, 11 Drawing Sheets

Specification includes a Sequence Listing.

Figure 1

| MOR | Sequence (5' to 3') |
|---|---|
| DPD*2A WT probe | CACTTACGTTGTCTGTTTTTTTTTT-disulfide amide |
| DPD*2A MUT probe | CACTTATGTTGTCTGTTTTTTTTTT-disulfide amide |

Figure 2

| Synthetic DNA samples | Sequence (5' to 3') |
|---|---|
| DPD*2A WT/MUT target | CATATTGGTG TCAAAGTGTC ACTGAACTAA AGGCTGACTT TCCAGACAAC G/A TAAGTGTGAT TTAACATCTA AAACAAGAGA ATTGGCATAA GTTGGTGAAT |

Figure 3

| PCR primers | Sequence (5' to 3') | Amplicon size (nt) |
|---|---|---|
| DPD-Forward | AGTGAGAAAACGGCTGCATAT | 118 |
| DPD-Reverse | CATTCACCAACTTATGCCAATTCTCTT | |

Figure 4

| Initial denaturing | 95°C | 3 min |
|---|---|---|
| 10-cycle touchdown | 95°C | 20 sec |
| | 60°C, -0.5°C/cycle | 20 sec |
| | 72°C | 25 sec |
| 40-cycle amplification | 95°C | 20 sec |
| | 55°C | 20 sec |
| | 72°C | 25 sec |
| End | 4°C | Hold |

Figure 5
(a)
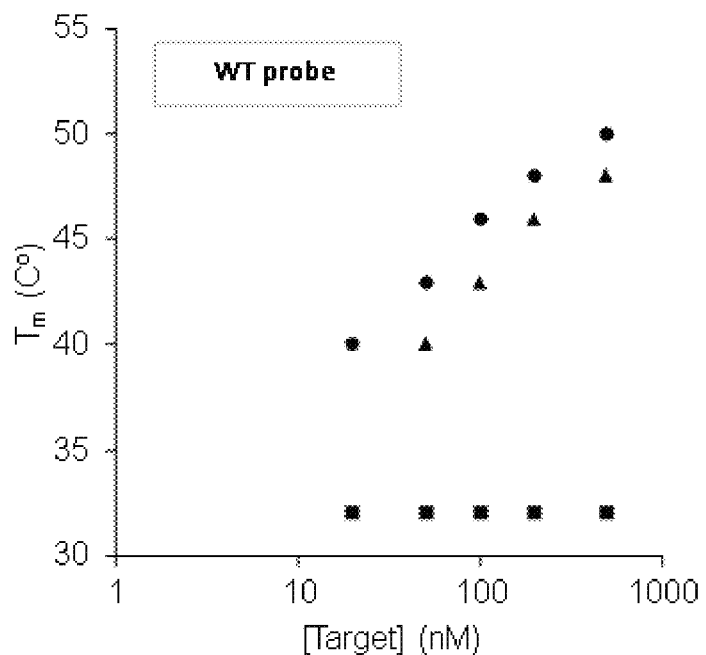
(b)
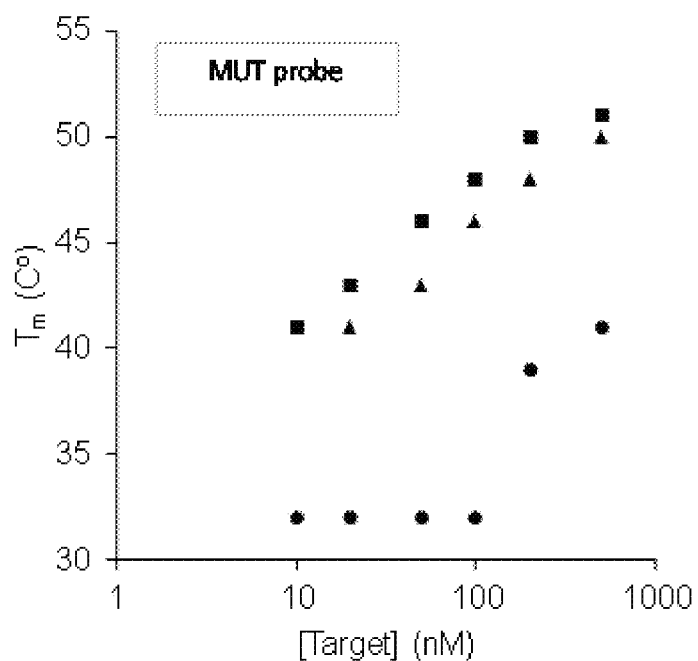

Figure 7

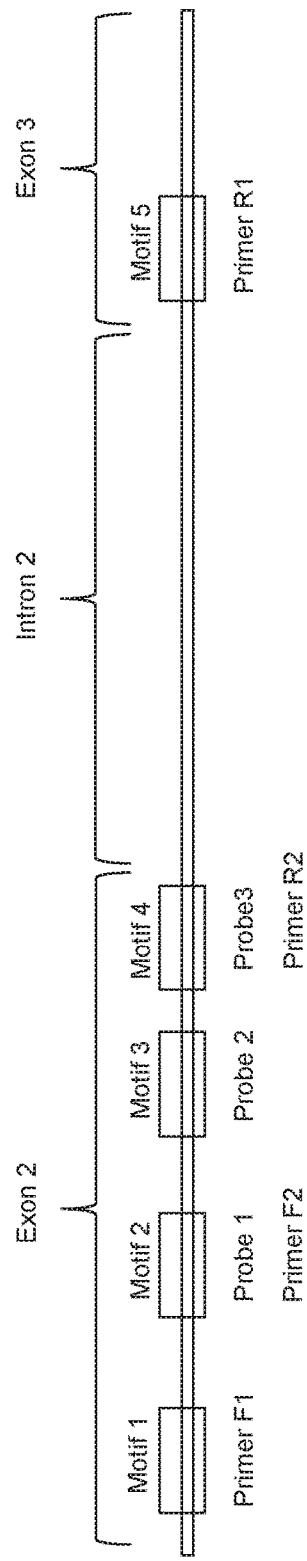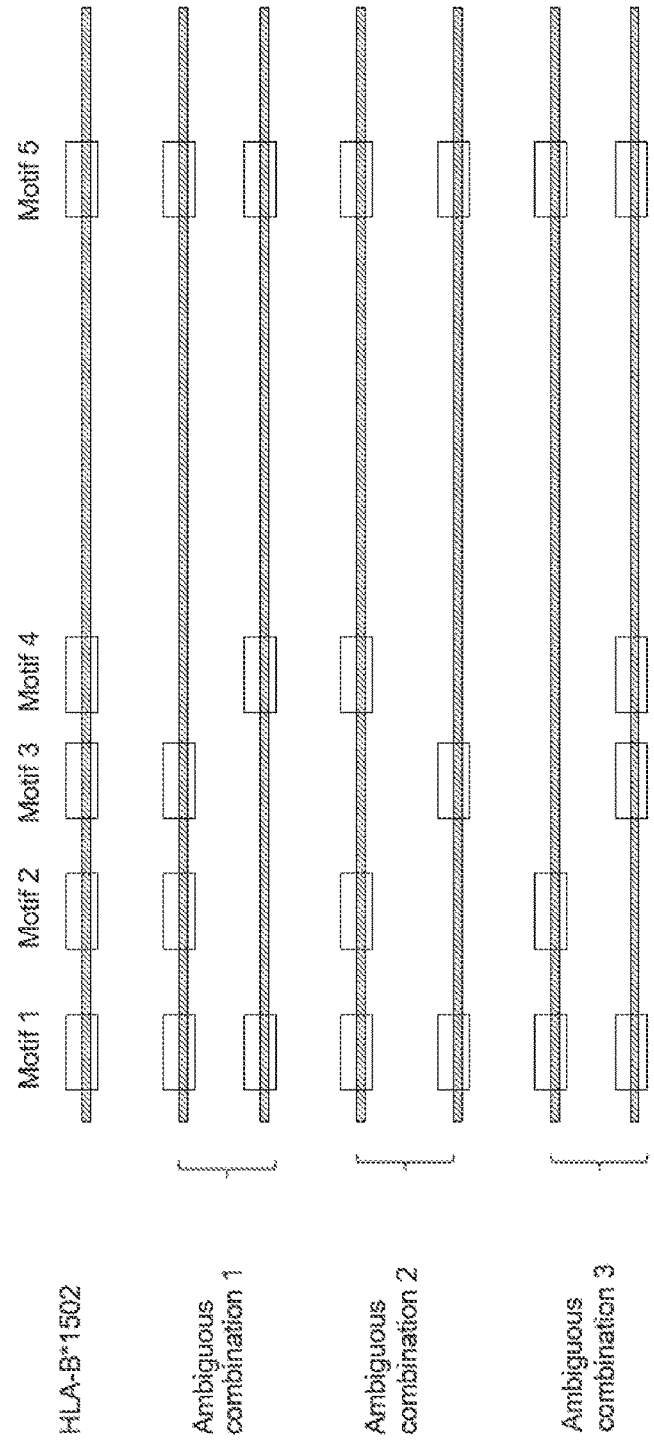

Figure 10

| MOR | Sequence (5' to 3') |
|---|---|
| Probe 1 | GTGTTCCGATCCCAATTTTTTTTTT-disulfide amide |
| Probe 2 | TGGTCTTGGAGATCTTTTTTTTTT-disulfide amide |
| Probe 3 | AGGTTCCGCAGGCTTTTTTTTTTT-disulfide amide |
| GAPDH probe | CAAGCTTCCCGTTCTCAGCCTTTTT-disulfide amide |

Figure 11

| Synthetic DNA samples | Sequence (5' to 3') |
|---|---|
| Probe1 PM | AGG AGG GGC CGG AGT ATT GGG ACC GGA ACA CAC AGA TCT CCA AGA CCA ACA CAC A |
| Probe1 MM | AGG AGG GGC CGG AGT ATT GGG ACC GGG AGA CAC AGA TCT CCA AGA CCA ACA CAC A |
| Probe2 PM | GGC CGG AGT ATT GGG ACC GGA ACA CAC AGA TCT CCA AGA CCA ACA CAC |
| Probe2 MM1 | GGC CGG AGT ATT GGG ACC GGA ACA CAC AGA TCT GCA AGA CCA ACA CAC |
| Probe2 MM2 | GGC CGG AGT ATT GGG ACC GGA ACA CAC AGA TCT TCA AGA CCA ACA CAC |
| Probe2 MM3 | GGC CGG AGT ATT GGG ACC GGA ACA CAC AGA TCT ACA AGA CCA ACA CAC |
| Probe3 PM | AGACTTACCG AGAGAGCCTG CGGAACCTGC GCGGCTACTA |
| Probe3 MM | AGACTTACCG AGAGAGCCTG CGGACCCTGC TCCGCTACTA |

- P4 positive: valid test
- P1, P2-1, P2-2, P3, P4 all positive: HLA-B*1502 carrier

| PCR primers | Sequence (5' to 3') | Amplicon size (nt) |
|---|---|---|
| PCR1-F | CGC GAGTCC GAG GAT GGC | 431 |
| -R | CG CAG CCA TAC ATC CTC TGG ATGA | |
| PCR2-F | GGA GTA TTG GGA CCG GAAC | 88 |
| -R | GTT GTA GTA GCC GCG CAG GT | |
| GAPDH-F | GGAAGGTGAAGGTCGGAGTC CTC | 231 |
| -R | CCTGGAAGATGGTGATGGGATTTC | |

| Initial denaturing | 95°C | 2 min |
|---|---|---|
| 45-cycle touchdown | 95°C | 30 sec |
| | 67°C | 30 sec |
| | 72°C | 30 sec |
| 10-cycle amplification | 95°C | 20 sec |
| | 57°C | 20 sec |
| | 72°C | 30 sec |
| End | 4°C | Hold |

Figure 16
| MOR | Sequence (5' to 3') |
|---|---|
| CYP2C19*2 WT probe | GTTATGGGTTCC<u>C</u>GGTTTTTTTTTT-disulfide amide |
| CYP2C19*2 MUT probe | GTTATGGGTTCC<u>T</u>GGTTTTTTTTTT-disulfide amide |
Figure 17
(a)
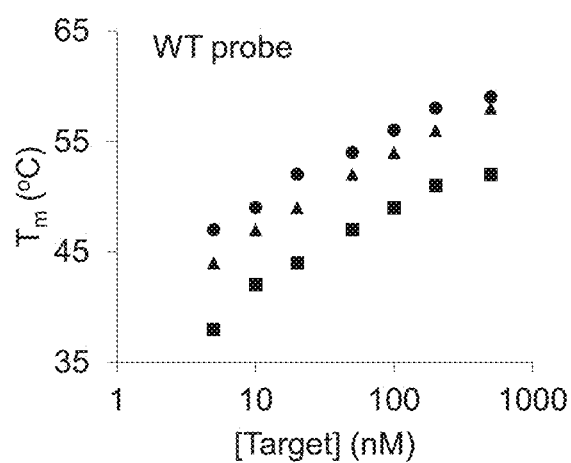
(b)
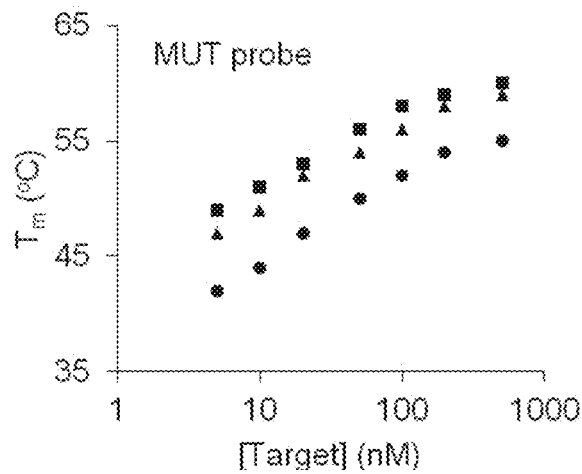

| Synthetic DNA samples | Sequence (5' to 3') |
|---|---|
| CYP2C19*2WT/MUT target | AGATATGCAATAATTTTCCCACTATCATTGATTATTTCCC<br>G/A<br>GGAACCCATAACAAATTACTTAAAAACCTTGCTTTTATGG |

| PCR primers | Sequence (5' to 3') | Amplicon size (nt) |
|---|---|---|
| SEQ ID NO:15<br>CYP2C19*2-Forward | TGCAATAATTTTCCCACTATCATTG | 93 |
| SEQ ID NO: 16<br>CYP2C19*2-Reverse | CTCCAAAATATCACTTTCCATAAAAGCA | |

Figure 21

| Initial denaturing | 95°C | 2 min |
|---|---|---|
| 10-cycle touchdown | 95°C | 20 sec |
| | 60°C, -0.5°C/cycle | 20 sec |
| | 72°C | 20 sec |
| 40-cycle amplification | 95°C | 15 sec |
| | 55°C | 15 sec |
| | 72°C | 20 sec |
| End | 4°C | Hold |

METHOD FOR DETECTION OF A GENETIC VARIANT

FIELD OF THE INVENTION

The present invention relates to the detection of genetic variants including methods and kits for detecting the same.

BACKGROUND OF THE INVENTION

Genetic variation among individuals within a population is often observed by phenotypic changes that in some cases manifest as a disease or disorder. There are some instances where a disease or disorder only manifests as an adverse reaction to an external stimulus such as a pharmaceutical drug or other chemicals. The association studies of adverse drug reactions (ADRs) and patients' genetic makeup hold the promise of greatly reducing the ADR-related morbidity and mortality by genetic testing. There are several known links between ADR and genetic variants.

Fluorouracil (5-FU) has been used as a chemotherapy agent in the treatment of patients with breast, colorectal, lung and other cancers for several decades. Side-effects of 5-FU include diarrhea, stomatitis, mucositis, neurotoxicity, and in some cases, death. These are largely due to genetic inability to metabolize the drug. Dihydropyrimidine dehydrogenase (DPD), an enzyme encoded by the DPD gene, is responsible for the elimination of ~80% of the standard dose of 5-FU. DPD deficiency due to DPD gene mutations has been associated with severe 5-FU toxicity. It has been found that ~3-5% of patients harbor at least a partial DPD deficiency. The most common mutation associated with DPD deficiency is IVS14+1 G>A, a G>A base change at the splice recognition sequence of intron 14 (known as DPD*2A). This single-nucleotide variation leads to exon skipping and results in a 165-bp deletion in the DPD mRNA. A homozygote DPD*2A genotype results in complete deficiency, while the heterozygous DPD*2A genotype results in partial deficiency of DPD. The pre-therapeutic detection of this metabolic dysfunction could prevent severe side-effects of 5-FU by administering alternative treatments.

Similarly, the linkage of CYP2C19 genotype with clinical outcomes among clopidogrel-treated acute coronary syndrome (ACS) patients, particularly those undergoing percutaneous coronary intervention (PCI) has been reported. Clopidogrel is a commonly prescribed oral, antiplatelet agent used to inhibit blood clots in coronary artery disease, peripheral vascular disease, and cerebrovascular disease. As a thienopyridine prodrug, clopidogrel requires hepatic biotransformation to form an active metabolite. The hepatic CYP2C19 enzyme is one of CYP450 superfamily members that is involved in the metabolism of clopidogrel. The CYP2C19 gene is highly polymorphic with over 25 known variant alleles. The most common CYP2C19 loss-of-function allele is CYP2C19*2 (c.681G>A; rs4244285), with allele frequencies of ~15% in Caucasians and Africans, and 29-35% in Asians. However, current genetic testing methods for loss of function generally require expensive instruments and long turnaround time.

Another example is the discovery of the strong linkage between carbamazepine-induced Steven Johnson Syndrome/Toxic Epidermal Necrolysis (SJS/TEN) and a specific allele of human leukocyte antigen (HLA), HLA-B*1502. Carbamazepine is the first-line drug for treatment of patients with epilepsy, neuropathic pain and bipolar disorder. However, carbamazepine therapy may cause dangerous or even fatal skin reactions, such as SJS and TEN in patients with the HLA-B*1502 allelic variation. Prevalence of the HLA-B*1502 allele in Asian populations, except in Japanese and Koreans, is much higher than in Caucasian and African populations. Some studies revealed that the negative predictive value of HLA-B*1502 test for carbamazepine-induced SJS could be close to 100%. HLA-B gene is highly polymorphic with more than 2000 unique alleles, which complicates the determination of a specific allele. Sanger sequencing is considered to be the gold standard for HLA typing. However, the phase ambiguity often causes problems for SBT in identification of allele combinations. Next-generation sequencing (NGS) technologies are able to obtain the sequence of a single DNA molecule and may rule out the phase ambiguity, but drawbacks of the current NGS methods include the short read length, high workloads for library preparation and lengthy processing time. A recent report employed loop-mediated isothermal amplification (LAMP) for HLA-B*1502 screening (Cheng, et al. Clin. Chem. 2009, 55, 1568.). Unfortunately, the specificity of these methods is not sufficient to distinguish HLA-B*1502 from quite a few other alleles that are not rare in some populations. The false assays will rule out the patients with very low SJS risk from the effective carbamazepine therapy, and increase the treatment cost. Since the cost-effectiveness of HLA-B*1502 screening is highly dependent on the accuracy and cost of the genetic test, there is an urgent need for a new assay that is more specific and less costly.

The US Food and Drug Administration (FDA) and other regulatory bodies have required labelling of several drugs that may have adverse effects in certain genotypes. For Example a requirement for fluorouracil (5-FU)-based drugs is to contain a warning for hypersensitivity in some individuals. In another example, the US Food and Drug Administration issued an alert in 2007 that recommends screening of the HLA-B*1502 allele before starting treatment with carbamazepine for patients with ancestry from areas in which the specific allele is present. Similarly, the boxed warning on the clopidogrel label recommends consideration of alternative antiplatelet therapy in poor metabolizers with ACS or PCI.

Commercial kits for genotyping tests are available for some genetic variants and are used to predict an individual's tolerance or intolerance of a drug. The testing platforms used include Sanger sequencing and restriction fragment length polymorphism (RFLP) analysis. The assays based on these platforms are either time-consuming or costly, and therefore, less suitable for on-demand testing. Commercial kit based on real-time PCR is also available unfortunately, the specificity of these methods is not sufficient to distinguish complex allelic variants from quite a few other alleles that are not rare in some populations. Since the cost-effectiveness of screening is highly dependent on the accuracy and cost of the genetic test, there is an urgent need for a new assay that is more specific and less costly.

SUMMARY OF THE INVENTION

The present invention meets this need by providing, in a first aspect of the invention, a method of detecting a genetic variant associated with a disease or disorder, including incompatibility with a pharmaceutical, the method comprising the steps of a) providing a first nano-particle coupled to at least one morpholino nucleic acid probe comprising a target-complementary region comprising a base sequence that is a perfect match to the genetic variant;

b) combining a sample containing nucleic acid suspected of containing the genetic variant and the first nano-particle to provide a first mixture under conditions that allow hybridization of the morpholino nucleic acid probe and the nucleic acid suspected of containing the genetic variant;
c) sequentially heating the first mixture and determining the melting temperature of the hybridization complex between the morpholino nucleic acid probe and the nucleic acid suspected of containing the genetic variant;
d) comparing the melting temperature determined in step c) with a standard to determine whether the sample comprises nucleic acid containing the genetic variant.

Another aspect of the invention relates to a detection kit for performing the methods described herein, comprising: a first nano-particle coupled to at least one morpholino nucleic acid probe comprising a target complimentary region comprising a base sequence that is a perfect match to a genetic variant sequence associated with a disease or disorder, including incompatibility with a pharmaceutical.

Other aspects of the invention will be apparent to a person skilled in the art with reference to the following drawings and description of various non-limiting embodiments.

BRIEF DESCRIPTION OF THE DRAWINGS

The drawings are not necessarily drawn to scale, emphasis instead generally being placed upon illustrating the principles of various embodiments. In the following description, various embodiments of the invention are described with reference to the following drawings.

FIG. 1. Sequences of the MORs used in the DPD tests. The single-base differences for each pair of the probes are underlined. FIG. 1 corresponds to the following SEQ ID Nos.: SEQ ID Nos. 1 and 2.

FIG. 2. Sequences of the synthetic DNA samples used in the DPD genotyping analysis. The single-nucleotide polymorphism (SNP) positions are underlined. FIG. 2 corresponds to the following SEQ ID Nos.: SEQ ID No. 19.

FIG. 3. PCR primers for DPD target sequence amplification. FIG. 3 corresponds to the following SEQ ID Nos.: SEQ ID Nos. 9 and 10.

FIG. 4. Thermal cycler protocol for PCOR amplification of DPD sequences.

FIG. 5. Melting temperature as a function of DPD target concentration for the (a) WT and (b) MUT probes targeting the DPD*2A SNP. Samples are synthetic single-stranded wild-type DNA (circle), mutant DNA (square), and their 1:1 mixture (triangle, representing heterozygote samples). Error of $T_m$ measurement=±1° C.

FIG. 7. Alignment of typical HLA-B alleles. FIG. 7 corresponds to the following SEQ ID Nos.: SEQ ID Nos. 20, 21, 22, 23, 24, 25, 26, 27, 28, 29, 30, 31, 32, 33, 34, 35, 36, 37, 38, 39, 40, 41, 42 and 43.

FIG. 8. PCR primer and probe design for HLA-B*1502 allele determination.

FIG. 9. Combination ambiguities in HLA-B alleles of PCR1.

FIG. 10. Sequences of the MORs used in the HLA-B tests. FIG. 10 corresponds to the following SEQ ID Nos.: SEQ ID Nos. 3, 4, 5 and 6.

FIG. 11. Sequences of the synthetic DNA samples used in the HLA-B genotyping analysis. The nucleotide variants are highlighted by underlining. FIG. 11 corresponds to the following SEQ ID Nos.: SEQ ID Nos. 44, 45, 46, 47, 48, 49, 50 and 51.

FIG. 13 corresponds to the following SEQ ID Nos.: SEQ ID Nos. 11, 12, 13, 14, 17 and 18.

FIG. 16. Sequences of the MORs used in the CYP2C19 tests. The single-base difference is highlighted by underlining. FIG. 16 corresponds to the following SEQ ID Nos.: SEQ ID Nos. 7 and 8.

FIG. 17. Melting temperature as a function of target concentration for the (a) WT and (b) MUT probes targeting the CYP2C19*2 SNP. Samples are synthetic single-stranded wild-type DNA (circle), mutant DNA (square), and their 1:1 mixture (triangle, representing heterozygote samples). Error of $T_m$ measurement=±1° C.

FIG. 18 corresponds to the following SEQ ID Nos.: SEQ ID No. 52.

FIG. 21. Thermal cycler protocol for CYP2C19 PCR amplification.

DETAILED DESCRIPTION

Figure 6:
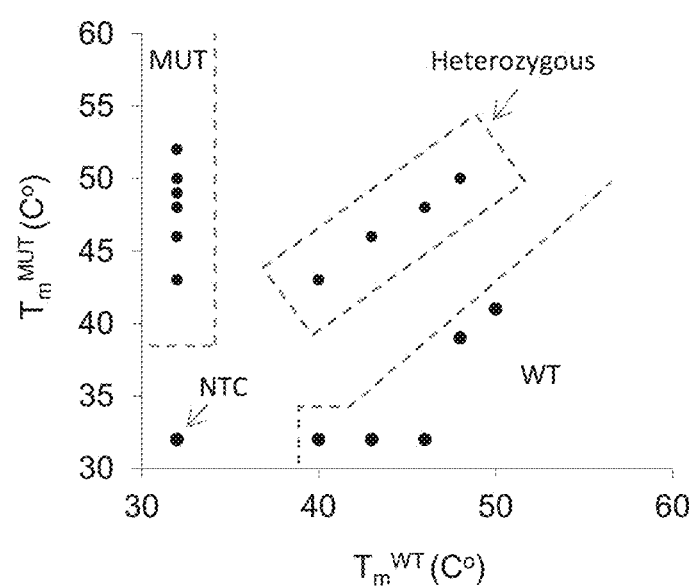
FIG. 6. Scatter plots of $T_m^{WT}$ and $T_m^{MUT}$ of the DPD synthetic DNA samples. Error of $T_m$ measurement=±1° C.

The inventors have developed a cost-effective genotyping platform using nanoprobes coupled to specific morpholino oligo sequences. The corresponding assay kit can greatly promote the translation of the pharmacogenomic knowledge in clinical practice.

A first aspect of the invention relates to a method of detecting a genetic variant associated with a disease or disorder, including incompatibility with a pharmaceutical, the method comprising the steps of
a) providing a first nano-particle coupled to at least one morpholino nucleic acid probe comprising a target-complementary region comprising a base sequence that is a perfect match to the genetic variant;
b) combining a sample containing nucleic acid suspected of containing the genetic variant and the first nano-particle to provide a first mixture under conditions that allow hybridization of the morpholino nucleic acid probe and the nucleic acid suspected of containing the genetic variant;
c) sequentially heating the first mixture and determining the melting temperature of the hybridization complex between the morpholino nucleic acid probe and the nucleic acid suspected of containing the genetic variant;
d) comparing the melting temperature determined in step c) with a standard to determine whether the sample comprises nucleic acid containing the genetic variant.

The term "genetic variant" as used herein refers to a naturally occurring gene sequence that deviates from a predominant genotype of a population resulting in a variation of a phenotype associated with a disease or disorder, including incompatibility with a pharmaceutical drug. The predominant genotype may be defined to be that sequence which is present in a majority of the population or the most frequent genotype. In various embodiments, the predominant genotype comprises the same gene sequence in at least 55% of the population, or at least 60%, or at least 70%, or at least 80%, or at least 90%, or at least 95% of the population. Herein, the term "predominant genotype" is also referred to as the "wildtype". Accordingly, the wildtype or predominant sequence does not comprise the genetic variation that is responsible for the disease or disorder. Examples of genetic variants include deletions of nucleic acids, addition of nucleic acids, single nucleotide polymorphism (SNP) or allelic variants. The term "genetic variant", as used herein, thus means a specific variation in the base sequence of a given gene.

The morpholino nucleic acids of the present invention are phosphorodiamidate morpholino oligonucleotides (PMO), wherein the sugar and phosphate backbone is replaced by morpholine groups linked by phosphoramidates, and the nucleobases, such as cytosine, guanine, adenine, thymine and uracil, preferably adenine, guanine, cytosine and thymine, are coupled to the morpholine ring. The PMOs typically comprise monomeric units of the structure:

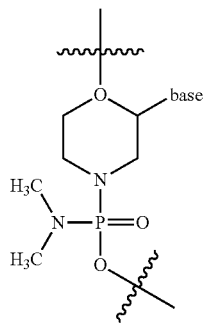

The terms "morpholino", "morpholino nucleic acid" and "morpholino oligo(nucleotide)" are used interchangeably herein and refer to the afore-mentioned phosphorodiamidate morpholino oligonucleotides (PMOs).

In various embodiments the morpholino oligo is covalently coupled to the nanoparticle. This may for example be achieved via the 5'-terminal phosphoramidate group or the 3'-terminal ring nitrogen. The length of the morpholino oligonucleotides described herein can comprise about 5 monomeric units to about 40 monomeric units; about 10 monomeric units to about 35 monomeric units; or about 15 monomeric units to about 35 monomeric units.

As used herein, the term "complementary" or "complementarity" relates to the relationship of nucleotides/bases on two different strands of DNA or RNA, or the relationship of nucleotides/bases of the base sequence of the morpholino and a DNA/RNA strand, where the bases are paired by Watson-Crick base pairing, i.e. guanine with cytosine, adenine with thymine (DNA) or uracil (RNA). Accordingly, the morpholino as described herein comprises a base sequence that can form hydrogen bond(s) with a target nucleotide sequence, for example a DNA or RNA sequence, by conventional Watson-Crick base pairing between complementary bases.

In this context, the term "hybridize" or "hybridization" refers to the interaction between two different strands of DNA or RNA or between nucleotides/bases of the base sequence of the morpholino and a DNA/RNA sequence by hydrogen bonds in accordance with the rules of Watson-Crick DNA complementarity.

A target-complementary region is a base sequence that has complementarity to a given target sequence and hybridizes to said target under conditions that allow such hybridization. "Perfectly matched", as used in this connection, refers to the feature that a base sequence is 100% complementary to the target nucleic acid sequence, i.e. all bases of the given sequence, for example the target-complementary region, form Watson-Crick base pairs with a contiguous nucleotide sequence in the target.

The term "nanoparticle" as used herein refers to any particle having a size from about 1 to about 250 nm as long as the nanoparticle is capable of providing optical properties; for example, generate optical signals sensitive to hybridization reactions. The diameter of the nanoparticle as described herein can range in the size from about 1 nm to about 250 nm; about 1 nm to about 200 nm; about 1 nm to about 160 nm; about 1 nm to about 140 nm; about 1 nm to about 120 nm; about 1 nm to about 80 nm; about 1 nm to about 60 nm; about 1 nm to about 50 nm; about 5 nm to about 250 nm; about 8 nm to about 250 nm; about 10 nm to about 250 nm; about 20 nm to about 250 nm; about 30 nm to about 250 nm; about 40 nm to about 250 nm; about 85 nm to about 250 nm; about 100 nm to about 250 nm; or about 150 nm to about 250 nm. In some embodiments, the diameter of the diameter of the nanoparticle is in the range of about 1 nm to about 100 nm.

In certain embodiments, the nanoparticle is a metal nanoparticle. In other embodiments, the nanoparticle is a colloidal metal.

In some embodiments, the metal is a noble metal. Non-limiting examples of a noble metal that can be used can include silver, gold, platinum, palladium, ruthenium, osmium, iridium or mixtures thereof, not to mention a few. Other metals that can also be used in the formation of the nanoparticle can include but are not limited to aluminium, copper, cobalt, indium, nickel, or any other metal amenable to nanoparticle formation). The nanoparticle as described herein can also comprise a semiconductor (including for example and without limitation, CdSe, CdS, and CdS or CdSe coated with ZnS) or magnetic (for example, ferromagnetite) colloidal materials. Other nanoparticles useful in the practice of the invention include, also without limitation, ZnS, ZnO, Ti, $TiO_2$, Sri, $SnO_2$, Si, $SiO_2$, Fe, Ag, Cu, Ni, Al, steel, cobalt-chrome alloys, Cd, titanium alloys, AgI, AgBr, $HgI_2$, PbS, PbSe, ZnTe, CdTe, $In_2S_3$, $In_2Se_3$, $Cd_3P_2$, $Cd_3As_2$, InAs, and GaAs.

Methods of making ZnS, ZnO, $TiO_2$, AgI, AgBr, $HgI_2$, PbS, PbSe, ZnTe, CdTe, $In_2S_3$, $In_2Se_3$, $Cd_3P_2$, $C_3As_2$, InAs, and GaAs nanoparticles are also known in the art. See for e.g., Weller, Angew. Chem. Int. Ed. Engl., 32, 41 (1993); Henglein, Top. Curr. Chem., 143, 113 (1988). Methods for making metal, semiconductor and magnetic nanoparticles are also well-known in the art, see for example, Ahmadi, T. E. et al., Science, 272, 1924 (1996); Henglein, A. et al., J. Phys. Chem., 99, 14129 (1995). Suitable nanoparticles are also commercially available from, for example, Ted Pella, Inc. (gold), Amersham Corporation (gold) and Nanoprobes Inc (gold). The nanoparticles comprising materials described herein are available commercially or they can be produced from progressive nucleation in solution (e.g., by colloid reaction), or by various physical and chemical vapour deposition process, such as sputter disposition. The nanoparticles as described herein can also be produced using $HAuCl_4$ and a citrate-reducing agent, using methods known in the art (see for example, Grabar, K. C. et al, Anal. Chem., 1995, 67, 735-743).

The morpholino oligo can be coupled to the nanoparticle by any suitable means. The coupling is preferably covalent coupling. It is further preferred that each nanoparticles comprises at least one, preferably more than one probe coupled to its surface. The coupling may for example be done by functionalizing the oligo with a group that can react with a given nanoparticle. In case the nanoparticle is a gold nanoparticle, the functional group can, without limitation, be a sulfur-containing group, such as a sulfide or thiol group.

The combining step may be done by combining the sample with the nanoparticles, preferably in form of a dispersion in an aqueous medium, under conditions that allow hybridization of the probe coupled to the nanoparticle to the target nucleic acid. These conditions may include the use of suitable buffers and temperature conditions, for example heating to a temperature that dissociates existing double-stranded structures and cooling to allow hybrid formation. The conditions may be strict to avoid hybridization with non-target nucleic acids. Typical conditions, including buffers and temperature conditions, for probe-target hybridization are well-known in the art.

The sample may be any suitable sample, but is preferably a biological sample that contains nucleic acid molecules. Such samples may, for example, be derived from tissues and body fluids or any other biological samples that contain cells or cell components. The term "body fluid", as used in this connection, includes blood, plasma, serum, lymph fluid and the like. Typically, the biological sample is a sample that contains intact cells, such as a mouth swap. The sample may be processed before being used in the described methods, for example subjected to various isolation/purification steps, all of which are known to those skilled in the art.

Melting temperature as used herein is the temperature at which a complex of the morpholino oligo and a nucleic acid dissociate into single stranded state. Thermal denaturation referred to as melting, comprises heating double stranded duplexes to break the hydrogen bonds formed between bases after which the two strands separate. Due to different molecular geometrics of nucleotides, a single inconsistency between the two strands will make binding between them less energetically favourable. This will result in perfect matched bases melting at a higher temperature than mismatched strands. A morpholino oligo with a perfect match to the genetic variant is typically designed such that it will however hybridize to both the genetic variant and the wildtype sequences, but the temperature at which the morpholino oligo dissociates from the genetic variant nucleic acid sequence will be higher than the temperature at which the morpholino oligo dissociates from the wildtype nucleic acid sequence. Similarly, where a morpholino oligo is a perfect match to the wildtype sequence it will hybridise to both the genetic variant and the wildtype sequences, but the temperature at which the morpholino oligo dissociates from the genetic variant nucleic acid sequence will be lower than the temperature at which the morpholino oligo dissociates from the wildtype nucleic acid sequence.

To determine the melting temperature, the hybridized complexes that form between the morpholino oligo probes and the nucleic acids are sequentially heated, for example by about one degree (° C.) in a given time interval. The melting temperature ($T_m$) is measured by means known in the art, for example change in absorbance intensity such as change in UV absorbance, alternatively by using intercalating fluorophores and measuring changes in fluorescence. In various embodiments, the melting temperature is indicated by a color change of the mixture upon dissociation of the probe and the sample nucleic acid. In these embodiments, because the signals can be visualized by the naked eye and/or recorded by a digital camera, no expensive detector is required. Thus, the method allows for rapid, convenient and cost-effective genetic testing.

Nobel metals exhibit variations in plasmon resonance due to changes in the local index of refraction. As small nanoparticles in solution, noble nanoparticles will appear as one colour and if they aggregate to form a larger cluster a colour change can be observed. In various embodiments gold nanoparticles are used together with the morpholino oligo probe whereby when the morpholino oligo is hybridised to a nucleic acid, the solution appears red and when the morpholino oligo is dissociated from the nucleic acid at the melting temperature, the nanoparticles aggregate and the solution appears grey. In other words the colour change is caused by the probe-target hybridization preventing aggregation of the particles, for example by sterically preventing the interaction between the individual particles, but once the target is dissociated, the interaction between the individual particles is no longer prevented and they aggregate. To achieve this switching between the non-aggregated state and the aggregated state, the nanoparticles comprising probes hybridized to the target may be subjected to conditions that would normally lead to particles aggregation but are insufficient to cause aggregation of the particles complexed with the target. Such conditions may, for example and without limitation, include buffer conditions with increased ionic strength, for example by high salt concentrations. Normally, such increased salt conditions lower the hydration of the nanoparticles and thus promote aggregation. However, in case the particles are complexed with the target the increase in ion strength is not sufficient to lead to aggregation so that aggregation only occurs once the nanoparticles are dissociated from the target nucleic acid.

Once the melting temperature has been determined, the obtained value is compared with a standard value which allows determination of the presence of the genetic variant. Depending on the type of standard, either an increase of the determined melting temperature compared to the standard or an equal value can indicate the presence of the genetic variant. If the presence of the genetic variant is indicated by an increase in melting temperature, the increase is preferably large enough to make specific detection possible. For example, the increase in melting temperature can be at least about 0.5° C., preferably at least about 1° C.

In various embodiments, the standard is established by determining the melting temperature of a complex of the first nano-particle coupled to at least one morpholino nucleic acid probe comprising a target-complementary region comprising a base sequence that is a perfect match to the genetic variant and the corresponding wildtype nucleic acid, wherein when the comparison in step d) shows that the melting temperature determined in step c) is higher than the melting temperature of the complex of the first nano-particle and the wildtype nucleic acid, this is indicative that the sample comprises nucleic acid containing the genetic variant.

In other various embodiments, the standard is established by determining the melting temperature of a complex of a second nano-particle coupled to at least one morpholino nucleic acid probe comprising a target-complementary region comprising a base sequence that is a perfect match to the corresponding wildtype base sequence and the wildtype nucleic acid, wherein when the comparison in step d) shows that the melting temperature determined in step c) is equal to the melting temperature of the complex of the second nano-particle and the wildtype nucleic acid, this is indicative that the sample comprises nucleic acid containing the genetic variant.

In still further embodiments, the standard is established by determining the melting temperature of a complex of a second nano-particle coupled to at least one morpholino nucleic acid probe comprising a target-complementary region comprising a base sequence that is a perfect match to the corresponding wildtype base sequence with the nucleic acid containing the genetic variant, wherein when the comparison in step d) shows that the melting temperature determined in step c) is higher than the melting temperature of the complex of the second nano-particle and the nucleic acid containing the genetic variant, this is indicative that the sample comprises nucleic acid containing the genetic variant;

In various embodiments, the standard is established by using synthetic sequences for either the genetic variant nucleic acid or the wildtype nucleic acid sequence.

In various embodiments, the method further comprises the steps of establishing a standard by
a1) providing a second nano-particle coupled to at least one morpholino nucleic acid probe comprising a target-complementary region comprising a base sequence that is a perfect match to the corresponding wildtype base sequence of the genetic variant;
b1) combining a sample containing nucleic acid suspected of containing the genetic variant and the second nano-particle to provide a second mixture under conditions that allow hybridization of the morpholino nucleic acid probe and the nucleic acid suspected of containing the genetic variant; and
c1) sequentially heating the second mixture and determining the melting temperature of the hybridization complex between the morpholino nucleic acid probe and the nucleic acid suspected of containing the genetic variant; and
wherein step d comprises comparing the melting temperature determined in step c) with the melting temperature determined in step c1), wherein when the melting temperature determined in step c) is higher than the standard melting temperature determined in step c1), this is indicative that the sample comprises nucleic acid containing the genetic variant.

The detection is comparative and dependant on the most specific hybridization, such that when the genetic variant sequence is present in a sample taken from an individual then the perfectly complimentary morpholino base sequence of the first probe will have a more specific hybridization than a morpholino base sequence of the second probe perfectly complimentary to the wildtype sequence and will result in higher melting temperatures for the first probe. In contrast, when the genetic variant sequence is not present in a sample taken from an individual and the wildtype genetic sequence is present then the perfectly complimentary morpholino base sequence of the first probe will have a less specific hybridization than a morpholino base sequence of the second probe perfectly complimentary to the wildtype sequence and will result in lower melting temperatures for the first probe.

In various embodiments the genetic variant is associated with a SNP of the gene encoding dihydropyrimidine dehydrogenase (DPD), said SNP resulting in incompatibility with the pharmaceutical compound Fluorouracil.

The SNP of the gene encoding Dihydropyrimidine Dehydrogenase may include *2A (DPD*2A) or [cytochrome P450]2C19*2 genotypes In this particular embodiment, the morpholino nucleic acid probe optionally comprises a target-complementary region being fully complementary to a sequence related to said SNP of DPD and having the base sequence set forth in SEQ ID NO:1 (CACTTATGTTGTCTGTTTTTTTTTT) and the wild type morpholino nucleic acid probe comprises a target-complementary region being fully complementary to the wild type sequence having the base sequence set forth in SEQ ID NO:2 (CACTTACGTTGTCTGTTTTTTTTTT).

The analysis of the data using the DPD sequences leads to unambiguous genotype assignment.

In various embodiments the genetic variant is associated with a SNP of the gene encoding CYP2C19 enzyme, said SNP resulting in incompatibility of the pharmaceutical compound Clopidogrel.

The allelic variant of the gene encoding CYP2C19 enzyme may include CYP2C19*2 (c.681G>A; rs4244285).

In this particular embodiment the morpholino nucleic acid probe optionally comprises a target-complementary region being fully complementary to a sequence related to said SNP having the base sequence set forth SEQ ID NO:7 (GTTATGGGTTCCTGGTTTTTTTTTT) and the wild type morpholino nucleic acid probe comprises a target-complementary region being fully complementary to the wild type sequence having the base sequence set forth in SEQ ID NO:8 (GTTATGGGTTCCCGGTTTTTTTTTT).

In various embodiments the genetic variant is associated with the allelic variation of the gene encoding human leukocyte antigen, said allelic variant resulting in incompatibility of the pharmaceutical compound Carbamazepine.

The allele variant of the gene encoding human leukocyte antigen may includes Human Leukocyte Antigen-B*1502 (HLA-B*1502).

In this particular embodiment the morpholino nucleic acid probe optionally comprises a target-complementary region being fully complementary to an allelic variant having the base sequence set forth in SEQ ID NO:3 (GTGTTCCGATCCCAATTTTTTTTTT); SEQ ID NO:4 (TGGTCTTGGAGATCTTTTTTTTTT); and SEQ ID NO:5 (AGGTTCCGCAGGCTTTTTTTTTTTT).

In various embodiments the method may optionally comprises a further functionalized nano-particle comprising a morpholino nucleic acid probe comprising a target-complementary region being fully complementary to a housekeeping gene. In one such embodiment the housekeeping gene is GADPH having a morpholino sequence set forth in SEQ ID NO:6 (CAAGCTTCCCGTTCTCAGCCTTTTT). Such nanoparticle with a probe for a housekeeping gene may function as a positive control.

In various embodiments the method further comprises enriching and/or amplifying the nucleic acid suspected of containing the genetic variant prior to combining the nucleic acid with the first or the second nano-particle. The enrichment is preferably done by amplification, more preferably by using polymerase chain reaction (PCR) to amplify the stretch of the nucleic acid containing the target sequence, i.e. the sequence comprising the genetic variant. This provides the advantage that the minimum amount needed for detection can be generated in cases where the genetic variant exists in low copy number in cells or where only small sample volumes are available.

Two separate PCR reactions have been designed to gauge HLA-B1502 allele in a highly specific manner. The method shows unique features and superior performance as compared with other available techniques. Firstly, the assay is highly specific, ensuring accurate detection. Secondly, the nanoprobe technique allows for distinct colorimetric detection, greatly reducing the screening cost. As a result, the nanoprobe-based genetic testing provides a highly specific and less costly assay for the screening of HLA-B*1502.

In various embodiments when the genetic variant is associated with an SNP of the gene encoding dihydropyrimidine dehydrogenase (DPD), the nucleic acid is amplified using a primer pair comprising SEQ ID NO:9 (DPD-Forward AGTGAGAAAACGGCTGCATAT) and SEQ ID NO:10 (DPD-Reverse CATTCACCAACTTATGCCAAT-TCTCTT).

In various embodiments when the genetic variant is associated with the allelic variation of the gene encoding human leukocyte antigen, the nucleic acid is amplified with a primer pair comprising SEQ ID NO:11 (P1-Forward CGC GAGTCC GAG GAT GGC) and SEQ ID NO:12 (P1-Reverse CG CAG CCA TAC ATC CTC TGG ATGA) and/or SEQ ID NO:13 (P2-Forward GGA GTA TTG GGA CCG GAAC) and SEQ ID NO:14 (P2-Reverse GTT GTA GTA GCC GCG CAG GT).

In various embodiments when the genetic variant is associated with an SNP of the gene encoding CYP2C19 enzyme, the nucleic acid is amplified with a primer pair comprising SEQ ID NO:15 (Forward-TG-CAATAATTTTCCCACTATCATTG), and SEQ ID NO:16 (Reverse-CTCCAAAATATCACTTTCCATAAAAGCA).

In various embodiments the method further comprising the primer pair SEQ ID NO:17 (GAPDH-Forward GGAAGGTGAAGGTCGGAGTC CTC) and SEQ ID NO:18 (GAPDH-Reverse CCTGGAAGATGGT-GATGGGATTTC) for amplifying the housekeeping gene.

Another aspect of the invention relates to a detection kit for performing the methods described herein comprising: a first nano-particle coupled to at least one morpholino nucleic acid probe comprising a target complimentary region comprising a base sequence that is a perfect match to a genetic variant sequence associated with a disease or disorder, including incompatibility with a pharmaceutical.

In various embodiments the kit further comprises a second nano-particle coupled to at least one morpholino nucleic acid probe comprising a target complimentary region comprising a base sequence that is a perfect match to a wildtype sequence associated with a disease or disorder.

In various embodiments the target-complementary region of the first probe is selected from the group consisting of the base sequences set forth in SEQ ID Nos. 1, 3-5 and 7. In case the first probe has the base sequence of SEQ ID NO:1, the target-complementary region of the second probe may consist of the base sequence set forth in SEQ ID NO:2. In case the first probe has the base sequence of SEQ ID NO:7, the target-complementary region of the second probe may consist of the base sequence set forth in SEQ ID NO:8.

In various embodiments the kit further comprises a functionalized nano-particle comprising a morpholino nucleic acid probe comprising a target-complementary region that is fully complementary to a housekeeping gene.

In various embodiments the housekeeping gene preferably comprises GADPH having a morpholino sequence set forth in SEQ ID NO. 6 (CAAGCTTCCCGTTCTCAGC-CTTTTT).

In various embodiments the nanoparticle and the morpholino nucleic acids of the kit are as described above in connection with the methods of the present invention.

In various embodiments the genetic variant is associated with a SNP of the gene encoding dihydropyrimidine dehydrogenase (DPD), said deficiency resulting in incompatibility with the pharmaceutical compound Fluorouracil.

The SNP of the gene encoding Dihydropyrimidine Dehydrogenase may include *2A (DPD*2A) or [cytochrome P450]2C19*2 genotypes In this particular embodiment the morpholino nucleic acid probe optionally comprises a target-complementary region being fully complementary to a sequence related to said SNP and having the base sequence set forth in SEQ ID NO:1 (CACTTA$\underline{T}$GTTGTCTGTTTTTTTTT) and the wild type morpholino nucleic acid probe comprises a target-complementary region being fully complementary to the wild type sequence having the base sequence set forth in SEQ ID NO:2 (CACTTACGTTGTCTGTTTTTTTTTT).

The genetic information provided by the assay kit can be used to predict DPD deficiency, and consequently, the toxicity of Fluorouracil. The method is simple and more cost-effective than other genotyping technologies.

In various embodiments the genetic variant is associated with a SNP of the gene encoding CYP2C19 enzyme, said SNP resulting in incompatibility of the pharmaceutical compound Clopidogrel.

The SNP of the gene encoding CYP2C19 enzyme may include CYP2C19*2 (c.681G>A; rs4244285).

In this particular embodiment the morpholino nucleic acid probe optionally comprises a target-complementary region being fully complementary to a sequence related to said SNP having the base sequence set forth in SEQ ID NO:7 (GT-TATGGGTTCC$\underline{T}$GGTTTTTTTTT) and the wild type morpholino nucleic acid probe comprises a target-complementary region being fully complementary to the wild type sequence having the base sequence set forth in SEQ ID NO:8 (GTTATGGGTTCCCGGTTTTTTTTT).

In various embodiments the genetic variant is associated with an allelic variation of the gene encoding human leukocyte antigen, said allelic variant resulting in incompatibility of the pharmaceutical compound Carbamazepine.

The allele variant of the gene encoding human leukocyte antigen may includes Human Leukocyte Antigen-B*1502 (HLA-B*1502).

In this particular embodiment the morpholino nucleic acid probe optionally comprises a target-complementary region being fully complementary to an allelic variant having the base sequence set forth in SEQ ID NO:3 (GTGTTCCGATC-CCAATTTTTTTTT); SEQ ID NO:4 (TGGTCTTGGA-GATCTTTTTTTTTT); and SEQ ID NO:5 (AGGTTC-CGCAGGCTTTTTTTTTT).

In various embodiments the kit may further comprise a functionalized nano-particle comprising a morpholino nucleic acid probe being a perfect match to a wild type sequence associated with a compatibility of the pharmaceutical.

In various embodiments the kit further comprises a primer pair for amplification of a nucleic acid prior to detection with the nanoparticles.

In various embodiments the primer pair is selected from the group consisting of SEQ ID NO:9 (DPD-Forward AGT-GAGAAAACGGCTGCATAT) and SEQ ID NO:10 (DPD-Reverse CATTCACCAACTTATGCCAATTCTCTT) SEQ ID NO:11 (P1-Forward CGC GAGTCC GAG GAT GGC) and SEQ ID NO:12 (P1-Reverse CG CAG CCA TAC ATC CTC TGG ATGA) and/or SEQ ID NO:13 (P2-Forward GGA GTA TTG GGA CCG GAAC) and SEQ ID NO:14 (P2-Reverse GTT GTA GTA GCC GCG CAG GT) SEQ ID NO:15 (Forward-TGCAATAATTTTCCCACTATCATTG), and SEQ ID NO:16 (Reverse-CTCCAAAATATCACTTTC-CATAAAAGCA).

In various embodiments wherein when the genetic variant is associated with the SNP of the gene encoding dihydropyrimidine dehydrogenase (DPD), said SNP resulting in incompatibility with the pharmaceutical compound Fluorouracil the primer pair comprises SEQ ID NO:9 (DPD-Forward AGTGAGAAAACGGCTGCATAT) and SEQ ID NO:10 (DPD-Reverse CATTCACCAACTTATGCCAAT-TCTCTT).

In various embodiments wherein when the genetic variant is associated with the allelic variation of the gene encoding human leukocyte antigen, said allelic variant resulting in incompatibility of the pharmaceutical compound Carbamazepine the primer pair comprises SEQ ID NO. 11 (P1-Forward CGC GAGTCC GAG GAT GGC) and SEQ ID NO. 12 (P1-Reverse CG CAG CCA TAC ATC CTC TGG ATGA) and/or SEQ ID NO. 13 (P2-Forward GGA GTA TTG GGA CCG GAAC) and SEQ ID NO. 14 (P2-Reverse GTT GTA GTA GCC GCG CAG GT).

In various embodiments wherein when the genetic variant is associated with the SNP of the gene encoding CYP2C19 enzyme, said SNP resulting in incompatibility of the pharmaceutical compound Clopidogrel the primer pair comprises SEQ ID NO. 15 (Forward-TGCAATAATTTTTC-CCACTATCATTG), and SEQ ID NO. 16 (Reverse-CTCCAAAATATCACTTTCCATAAAAGCA).

In various embodiments where the housekeeping gene comprises GAPDH, the kit further comprises the primer pair SEQ ID NO. 17 (GAPDH-Forward GGAAGGT-GAAGGTCGGAGTC CTC) and SEQ ID NO. 18 (GAPDH-Reverse CCTGGAAGATGGTGATGGGATTTC).

In various embodiments the kit further comprises the primer pair SEQ ID NO. 17 (GAPDH-Forward GGAAGGT-GAAGGTCGGAGTC CTC) and SEQ ID NO. 18 (GAPDH-Reverse CCTGGAAGATGGTGATGGGATTTC) for amplifying a housekeeping gene GAPDH.

The resulting kit may be highly specific and cost-effective screening of HLA-B*1502 or other genetic variants specific to the morpholinos sequences used.

The kit can also comprise one or more solutions, for example a hybridization buffer. The hybridization buffer can for example include but is not limited to phosphate, citrate, Tris, Hepes (4-(2-hydroxyethyl)-1-piperazineethanesulfonic acid), TAPS (N-Tris(hydroxymethyl)methyl-3-aminopropanesulfonic acid), MOPS (3-(N-morpholino)propanesulfonic acid), and PIPES (Piperazine-1,4-bis(2-ethanesulfonic acid) buffers, hypersolutes (for example, mannosylglycerate) or any other buffer solution, optionally containing, denaturing agents, salts, inert polymers, surfactants, among others. The one or more solutions in the kit can also include any one of the electrolytes as described herein. The one or more solutions of the kit can be supplied in wells of one or more microplate(s), for example a 384-well microplate, or in containers for later application in the wells of the microplate(s).

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples.

EXAMPLES

Preparation of the Nanoprobes.

Preparation of the nanoprobes used in this study followed a protocol similar to that reported previously. Briefly, the MORs modified with disulfide amide at the 3' terminal (Gene Tools, LLC) were treated with dithiothreitol to reduce the disulfide bond, and purified by using an NAP-5 column (GE Healthcare). The gold nanoparticles (40 nm-diameter, ~0.1 nM, Ted Pella, Inc.) were mixed with ~2 □M of thiolated MORs, 10 mM of phosphate buffer (pH 7.5), and allowed to incubate at room temperature overnight. Next, the MOR-nanoparticle conjugates were washed for at least 5 times with a phosphate buffer solution (5 mM, pH 7.5) by centrifugation to remove the unreacted MORs. The nanoprobes obtained were stable for at least 6 months when stored at 4° C. Before use, the nanoprobe solution should be uniformly dispersed by vortex.

gDNA Extraction.

Human gDNA samples can be extracted from whole blood. The extraction can be performed with the use of the following commercial kit Gentra Puregene DNA extraction kit (Qiagen), according to the manufacturer's instruction. Quantity (ng/□l) and quality of the gDNA samples can be checked by absorbance measurements using Nanodrop 1000 (Thermo Scientific). The quality of the samples can be characterized by the ratio of absorbance at 260 nm and 280 nm (A260/A280 ratio), which typically varies from 1.6 to 2.0.

PCR.

The PCR solution with a final volume of 25 □L would typically contain ~10 ng of gDNA, 12.5 □L of 2× master mix (Fermentas or Promega), and 1 □M of the forward primer and 100 nM of the reverse primer. PCR cycling can be performed on the PTC-200 DNA Engine. The success of the PCR in producing specific-sized amplicons can be verified by running a 5 □L aliquot of the PCR products on a 1.5% agarose gel stained with SafeView™ dye.

$T_m$ Measurements.

The synthetic samples or the PCR products were mixed with the specific WT and MUT nanoprobes, respectively, following which, the $T_m$ values of the target-probe hybrids were measured with the thermal cycler. The temperature was increased starting from 32° C. at an interval of 1.0° C. At each temperature, the solution was allowed to incubate for 1 min prior to color visualization. When a clear color change from red to light grey was observed, the temperature was recorded as $T_m$.

Genotype Assignment.

The $T_m^{WT}$-$T_m^{MUT}$ scatter plots obtained with the synthetic DNA targets (FIG. 2) were used as the standard genotyping diagrams. The experimental data point ($T_m^{WT}$, $T_m^{MUT}$) of samples can be plotted in the diagram, and the genotype is easily determined by the region where the data point resided.

Detection of DPD Genetic Variants

A dual-nanoprobe genotyping assay gauging the DPD*2A mutation was developed. Two sets of nanoprobes, i.e., wild-type (WT) and mutant (MUT) probes were developed, by functionalizing gold nanoparticles with morpholino oligonucleotides (MORs). The oligo sequences are shown in FIG. 1. For the WT nanoprobes, the oligo sequence was perfectly matched with the WT DPD gene segment, while for the MUT nanoprobes, the oligo sequence was perfectly matched with the mutant allele. The nanoprobes were stably dispersed in 5 mM of phosphate buffer as a red solution (pH~8) for at least 6 months. However, the addition of 100 mM of NaCl would lead to irreversible aggregation of the nanoparticles, and the solution color would turn colorless within 1 min.

The presence of target DNA in solution could increase the stability of the nanoprobes due to the increase in surface negative charge of the nanoparticles upon DNA attachment. If the surface density of attached DNA was high enough, the nanoparticles would be stably dispersed even in the presence of 100 mM of NaCl. To reveal the thermodynamic property of the DNA-nanoprobe hybrids, melting temperature ($T_m$) was measured. At $T_m$, the dissociation of the DNA sequence from the nanoparticle surface would occur, destabilizing the nanoparticles and resulting in solution color change from red to light grey. The $T_m$ data were then used to determine the genotype of the samples.

To characterize the nanoprobes, $T_m$ data were measured in the presence of 100 mM of NaCl (final concentration) and synthetic DNA samples over a broad concentration range of 5 nM to 500 nM (FIGS. 2 and 5). At room temperature (~25° C.), the WT nanoprobes were stabilized by ≥20 nM of the WT targets and could not be stabilized by the MUT targets, while the MUT nanoprobes were stabilized by ≥10 nM of the MUT targets and ≥200 nM of the WT targets. Therefore, the WT and MUT probes exhibited detection limits of ~20 nM and ~10 nM for the perfectly matched (PM) targets, respectively, while for the single-base-mismatched (1 MM) targets, the sensitivity of both probes was much lower. This might be attributed to the difference in binding thermodynamics of the target/probe hybrids, which determined the surface density of the target DNA on nanoparticles. The higher binding affinity of the PM targets allowed for more sensitive detection. In the concentration range of 20 nM to 200 nM, the nanoprobes only responded to their PM targets. At target concentrations of ≥200 nM, the MUT nanoprobes responded to either the PM or MUT targets. The $T_m$ difference induced by a single-base mismatch between the target and the probe was ~11° C. For the heterozygote samples, the $T_m$ was determined by the PM concentration.

The data shown in FIG. 5 could be presented as a $T_m^{WT}$-$T_m^{MUT}$ scatter plot, which could serve as the standard genotyping diagram (FIG. 6). The diagram was divided into three regions according to the specific sequence type of the samples. For an unknown sample, once the data of $T_m$,WT and $T_m$MUT were obtained, the genotype could be assigned based on the region where the data point lay in the standard genotyping diagram.

For human genomic DNA (gDNA) samples, PCR amplification can be conducted to produce sufficient amount of the specific target sequence of the DPD gene since the detection sensitivity of the assay was ~10-20 nM. FIGS. 3 and 4 show the PCR primers and thermal cycling parameters. Following PCR, two aliquots of the PCR products can be directly mixed with WT and MUT nanoprobes, respectively, then $T_m$ values of the hybrids of WT probe/amplicon and MUT probe/amplicon can be measured. The obtained data point ($T_m$WT, $T_m$MUT) can be plotted in the standard genotyping diagram to determine the sample's genotype.

In summary, the dual-nanoparticle assay kit to gauge DPD*2A genotype only required a standard thermal cycler, which allowed for cost-effective detection. The highly specific plasmonic nanoprobes ensured the accurate genotyping based on colorimetric signals.

Detection of HLA-B Genetic Variants

Figure 7:
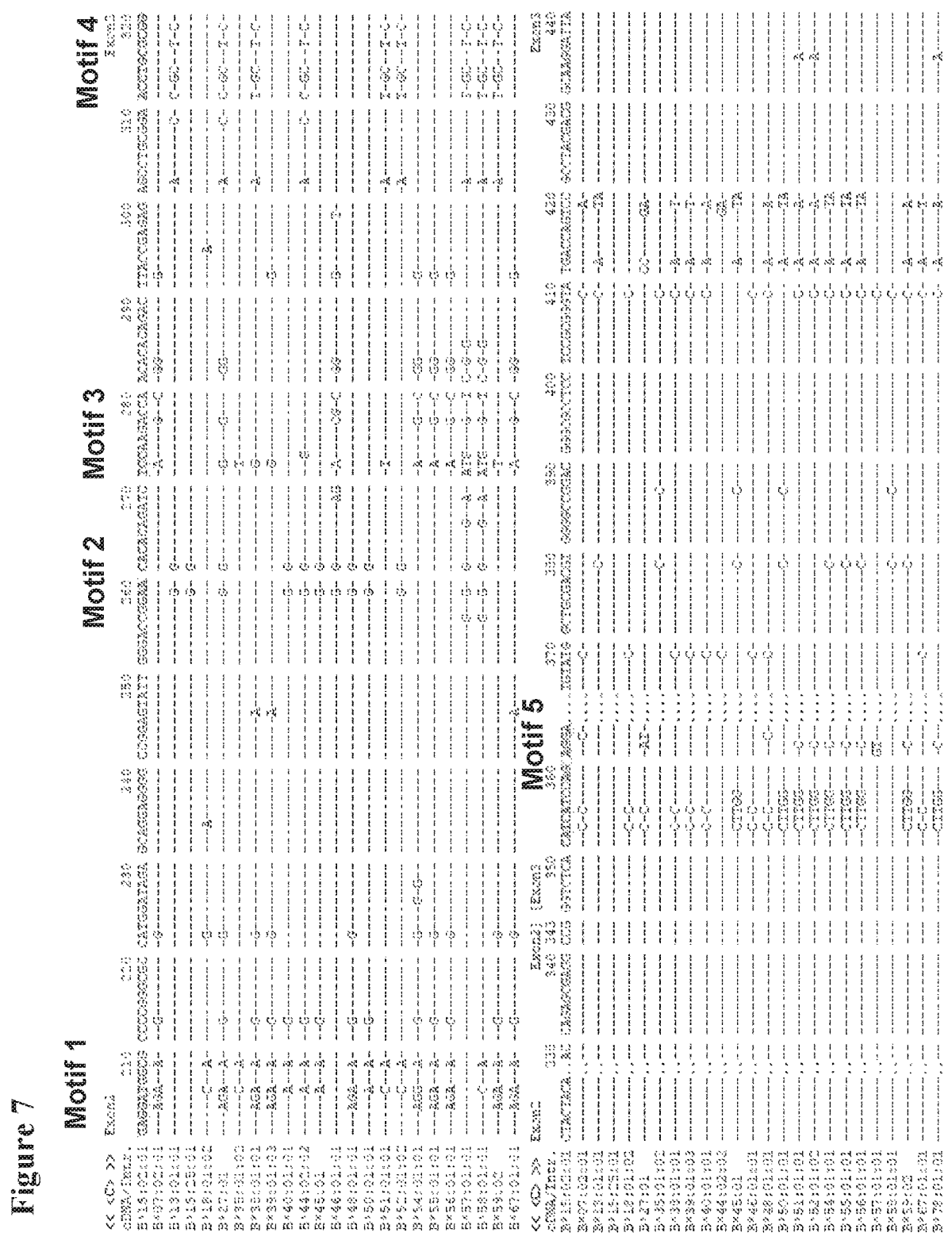

Five signature sequence motifs of HLA-B*1502 exons 2 and 3 have been used to identify the specific allele, as shown in FIG. 7. The presence of the five sequence motifs on a same DNA molecule indicates the carrier state of HLA-B*1502. The specificity of the method is relatively high. The alleles with across reactions with HLA-B*1502 include B*1588, B*15112, B*15121, B*15144, B*15170, B*15194, B*15213, 8*15214 and B*15223. These alleles are all very rare with no allele frequency reported in the world populations.

Two separate asymmetric PCR (aPCR) reactions were used to detect the HLA-B*1502 allele on the basis of the specificity of either the primers or the nanoprobes (FIG. 8). In the first aPCR reaction (PCR1), the forward primer (Primer F1) is specific to the sequence motif 1 and the reverse primer (Primer R1) is specific to the motif 5, while the motifs 2-4 are gauged by Probes 1-3, respectively. The amplicon size is 429 nt, covering part of exon 2, entire intron 2, and part of exon 3. The positive results of all the three nanoprobe assays indicate the presence of the five signature motifs, but with combination ambiguities as shown in FIG. 9. Therefore, a second PCR reaction (PCR2) is employed to achieve an unambiguous determination. In PCR2, the forward primer (Primer F2) is specific to motif 2, and the reverse primer (Primer R2) is specific to motif 4, while motif 3 is gauged by Probe 2. The positive result of the nanoprobe assay ensures the same phase of the three sequence motifs, ruling out the ambiguities shown in FIG. 3. An internal control (gauging the GAPDH gene) is included in PCR2 to monitor the validity of the PCR reactions.

The morpholino oligonucleotides (MORs) modified with disulfide amide at the 3' terminal, are shown in FIG. 10

Behavior of the Nanoprobes

Figures 12, 13:
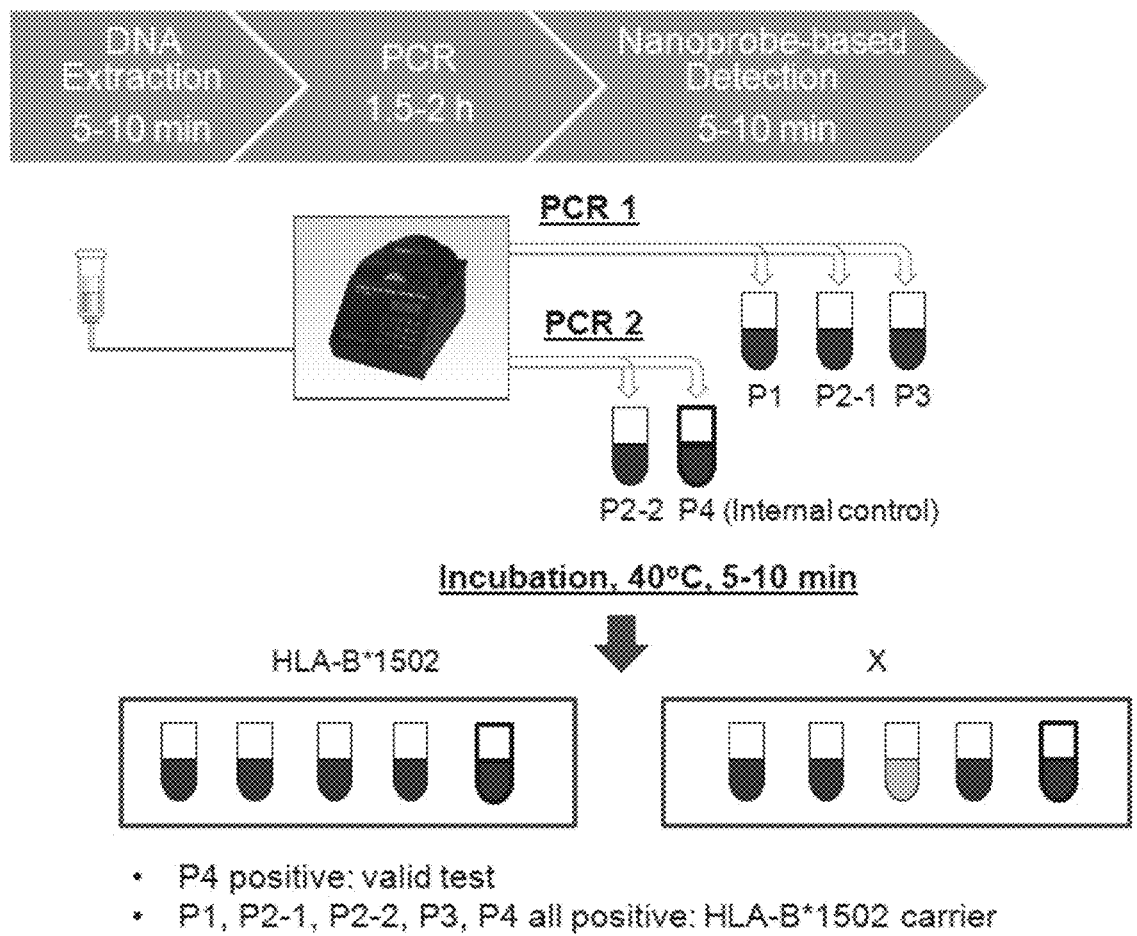
FIG. 12. Assay workflow of the HLA-B tests.
FIG. 13. Sequences of PCR primers used in the HLA-B tests.
Figures 14, 15:
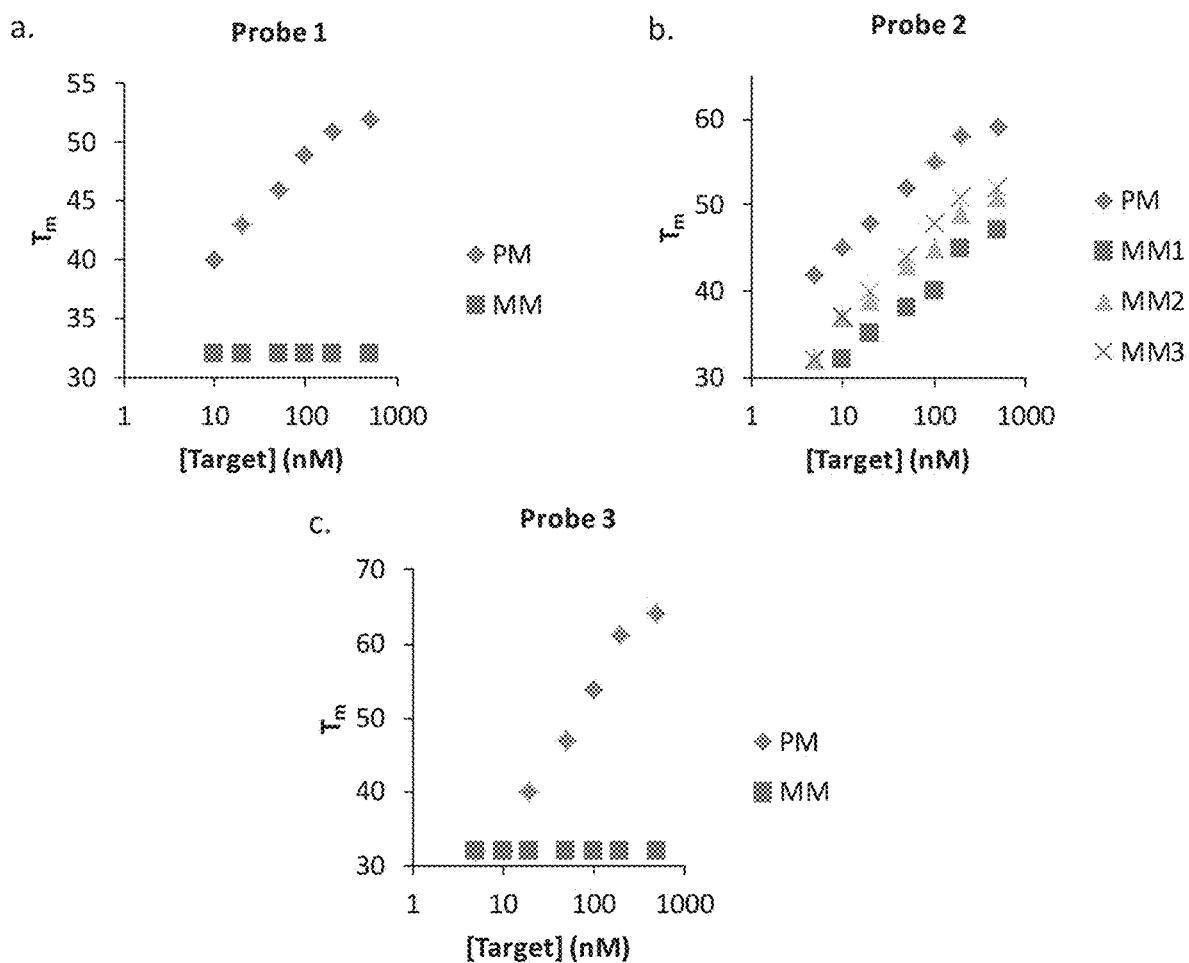
FIG. 14. Thermal cycler protocol for PCR amplification of HLA-B sequences.
FIG. 15. Melting temperature as a function of target concentration for nanoprobes 1, 2 and 3 for the HLA-B tests.

Nanoprobes were used to gauge three sequence motifs in this study. The ability of the nanoprobes to discriminate between the perfectly matched (PM) targets and the mismatched (MM) targets was examined by using synthetic oligonucleotide samples (FIG. 11). On the basis of the database, we selected sequences most similar to HLA-B*1502 signature motifs as mismatched (MM) samples. As shown in FIG. 4, most of the sequences could not generate signals over a wide concentration range (up to 500 nM) at temperatures higher than 32° C. For nanoprobe 2, single-base mismatches needed to be distinguished. FIG. 4 shows that the single-base mismatches generally reduced the $T_m$ by 8-10° C., allowing for allele discrimination HLA-B*1502 Genotype Determination Aliquots of the PCR1 products (ratio 1:1) were mixed with probes 1, 2 and 3 in three microtubes, respectively. Aliquots of the PCR2 products (ratio 1:1) were mixed with probe 2 and GAPDH probe in 2 microtubes, respectively. The mixed solutions were incubated at 40° C. for 5 min. If the GAPDH probe solution is red in color, the PCR reactions are valid. In this case, when all the other 4 solutions are red in color, the sample is HLA-B*1502 positive, otherwise, the sample is HLA-B*1502 negative. If the GAPDH probe solution becomes colorless, the assay is invalid and needs to be repeated. The assay workflow is shown in FIG. 12.

The nanoprobes were designed to be highly specific in recognition of nucleic acid targets, and generate colorimetric signals that can be easily visualized. This technology allows for accurate end-point detection with a simple workflow and standard equipment. On the basis of this platform, a cost-effective HLA-B*1502 screening kit was developed.

A simple nanoprobe-based assay has been developed for the HLA-B*1502 allele determination. The method shows unique features and superior performance as compared to other available techniques. Firstly, the assay is highly specific, ensuring accurate detection. Due to the large number of HLA-B alleles that are very close in sequence to the HLA-B*1502 allele and the high frequency of phase ambiguity, false positive commonly occurs in the screening of HLA-B*1502 carrier. Secondly, the nanoprobe technique allows for distinct colorimetric detection, greatly reducing the screening cost. The high specificity of the method is very important as it makes it accurate and cost effective. Analysis of the cost-effectiveness of HLA-B*1502 screening before carbamazepine treatment indicates that the genetic testing cost is critical, especially for the populations with low and medium prevalence of HLA-B*1502 allele. The visualizable signals simplify the detection, and exclude the requirement of expensive detectors. As a result, the nanoprobe-based genetic testing provides a specific and less costly assay for the screening of HLA-B*1502.

Detection of CYP2C19 Genetic Variants

Two sets of nanoprobes, i.e., wild-type (WT) and mutant (MUT) probes, were prepared by functionalizing gold nanoparticles with morpholino oligonucleotides (MORs). The MOR oligo sequences are shown in FIG. 16. The WT nanoprobe sequence is perfectly matched with the WT CYP2C19 gene segment, while the MUT nanoprobe sequence is perfectly matched with the CYP2C19*2 mutant allele. The as-prepared nanoprobes were red in color and stable for at least 6 months. However, irreversible aggregation of the nanoparticles could be induced by the addition of 500 mM of NaCl, causing the solution to change from red to light grey within 2 min.

When target DNA sequences were added in the nanoprobe solution, the nanoprobes became more stable even in the presence of 500 mM of NaCl, because DNA attachment increased the surface negative charge of the nanoparticles. As solution temperature was raised, the DNA-nanoprobe hybrids would be dissociated at the melting temperature ($T_m$), causing the nanoparticles to become unstable and changing the solution color from red to light grey. The value of $T_m$, could be obtained by visualizing the solution color change. The $T_m$ data were then used to determine the genotype of the samples.

Figures 18, 19, 20:
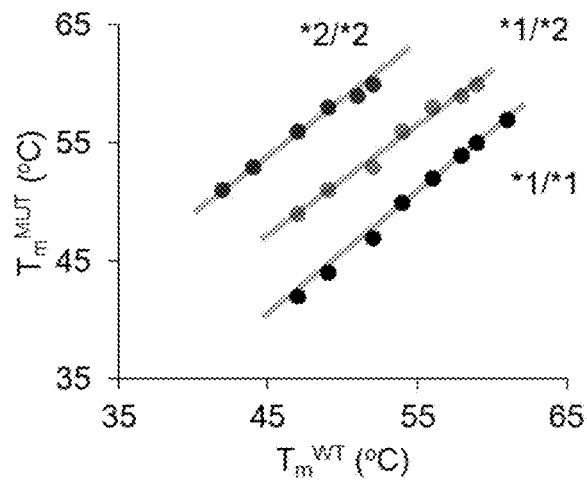
FIG. 18. Sequences of the CYP2C19 synthetic DNA samples used in this work. The SNP position is highlighted by underlining.
FIG. 19. Scatter plots of $T_m^{WT}$ and $T_m^{MUT}$ of the CYP2C19 synthetic DNA samples. Error of $T_m$ measurement=±1° C.
FIG. 20. PCR primers for CYP2C19 target sequence amplification.

FIG. 17 shows the nanoprobe behavior in response to synthetic DNA sequences (see FIG. 18). At room temperature (~25° C.), both of the WT and MUT nanoprobes were stabilized by ≥10 nM of the targets. The $T_m$ difference induced by a single-base mismatch between the target and the probe was ~5-7° C., For the heterozygote samples, the $T_m$ was determined by the perfectly matched target concentration.

FIG. 19 shows the data as a $T_m^{WT} T_m^{MUT}$ scatter plot, which could serve as the standard genotyping diagram. Three linear regions in the diagram are corresponding to the three genotypes, i.e. *1/*1, *1/*2 and *2/*2. For an unknown sample, once the data of $T_m^{WT}$ and $T_m^{MUT}$ were obtained, the genotype could be assigned based on the region where the data point lied in the standard genotyping diagram.

To test genomic DNA (gDNA) samples, PCR amplification of the gene sequence segments flanking the single nucleotide polymorphism (SNP) can be conducted by using primers shown in FIG. 20. The PCR thermal cycling parameters are shown in FIG. 21. Following PCR, two aliquots of the PCR products are mixed with the WT and MUT nanoprobes, respectively, then $T_m$ values of the hybrids of WT probe/amplicon and MUT probe/amplicon can be measured. The obtained data point ($T_m^{WT}$, $T_m^{MUT}$) can be plotted in the standard genotyping diagram to determine the sample's genotype.

In summary, a dual-nanoparticle assay kit to gauge CYP2C19*2 genotype was developed. The assay is cost-effective and accurate, and would be applicable for point-of-care testing.

The invention claimed is:

1. A detection kit for performing a method of detecting a genetic variant associated with a disease or disorder, including incompatibility with a pharmaceutical,
wherein the kit comprises a nano-particle coupled to at least one first morpholino nucleic acid probe comprising a target complimentary region comprising a base sequence that is a perfect match to the genetic variant sequence associated with the disease or disorder, including incompatibility with the pharmaceutical,
wherein the genetic variant is associated with a SNP of the gene encoding dihydropyrimidine dehydrogenase (DPD), said SNP resulting in incompatibility with the pharmaceutical fluorouracil; or the genetic variant is associated with a SNP of the gene encoding CYP2C19 enzyme, said SNP resulting in incompatibility of the pharmaceutical clopidogrel; or the genetic variant is associated with the allelic variation of the gene encoding human leukocyte antigen, said allelic variant resulting in incompatibility of the pharmaceutical carbamazepine.

2. The kit according to claim 1, further comprising a nano-particle coupled to at least one second morpholino nucleic acid probe comprising a target complimentary region base sequence that is a perfect match to a wildtype sequence associated with the disease or disorder.

3. The kit according to claim 1, wherein the target-complementary region of the first morpholino nucleic acid probe is selected from the group consisting of the base sequence set forth in SEQ ID NO:1; SEQ ID NO:7; SEQ ID NO:3; SEQ ID NO:4; and SEQ ID NO:5 and the target-complementary region of the second morpholino nucleic acid probe is selected from the group consisting of the base sequence set forth in SEQ ID NO:2; and SEQ ID NO:8.

4. The kit according to claim 1, further comprising a functionalized nano-particle comprising a morpholino nucleic acid probe comprising a target-complementary region that is fully complementary to a housekeeping gene.

5. The kit according to claim 4, wherein the housekeeping gene comprises GADPH having a morpholino sequence set forth in SEQ ID NO:6.

6. The kit according to claim 1, wherein the nanoparticle comprises a metal nanoparticle.

7. The kit according to claim 1, wherein the nanoparticle comprises a colloidal metal.

8. The kit according to claim 6, wherein the metal nanoparticle comprises a noble metal nanoparticle.

9. The kit according to claim 1, wherein the nanoparticle comprises a semiconductor or magnetic colloidal materials.

10. The kit according to claim 1, wherein the morpholino is covalently coupled to the nanoparticle.

11. The kit according to claim 1, wherein the morpholino comprises a sequence comprising about 10 monomeric units to about 35 monomeric units; or about 15 monomeric units to about 35 monomeric units.

12. The kit according to claim 1, wherein the kit further comprises a primer pair for amplification of a nucleic acid prior to detection with the nanoparticles.

13. The kit according to claim 12, wherein the primer pair is selected from the group consisting of:
SEQ ID NO:9 and SEQ ID NO:10;
SEQ ID NO:11 and SEQ ID NO:12;
SEQ ID NO:13 and SEQ ID NO:14; or
SEQ ID NO:15 and SEQ ID NO:16.

14. The kit according to claim 12, further comprising a primer pair SEQ ID NO:17 and SEQ ID NO:18 for amplifying a housekeeping gene GAPDH.

* * * * *

SEQUENCE LISTING

```
<160> NUMBER OF SEQ ID NOS: 52

<210> SEQ ID NO 1
<211> LENGTH: 25
<212> TYPE: DNA
<213> ORGANISM: Homo sapiens

<400> SEQUENCE: 1
cacttatgtt gtctgttttt ttttt                                         25

<210> SEQ ID NO 2
<211> LENGTH: 25
<212> TYPE: DNA
<213> ORGANISM: Homo sapiens

<400> SEQUENCE: 2
cacttacgtt gtctgttttt ttttt                                         25

<210> SEQ ID NO 3
<211> LENGTH: 25
<212> TYPE: DNA
```

```
<213> ORGANISM: Homo sapiens

<400> SEQUENCE: 3
gtgttccgat cccaattttt ttttt                                          25

<210> SEQ ID NO 4
<211> LENGTH: 25
<212> TYPE: DNA
<213> ORGANISM: Homo sapiens

<400> SEQUENCE: 4
tggtcttgga gatcttttt ttttt                                           25

<210> SEQ ID NO 5
<211> LENGTH: 25
<212> TYPE: DNA
<213> ORGANISM: Homo sapiens

<400> SEQUENCE: 5
aggttccgca ggcttttttt ttttt                                          25

<210> SEQ ID NO 6
<211> LENGTH: 25
<212> TYPE: DNA
<213> ORGANISM: Homo sapiens

<400> SEQUENCE: 6
caagcttccc gttctcagcc ttttt                                          25

<210> SEQ ID NO 7
<211> LENGTH: 25
<212> TYPE: DNA
<213> ORGANISM: Homo sapiens

<400> SEQUENCE: 7
gttatgggtt cctggttttt ttttt                                          25

<210> SEQ ID NO 8
<211> LENGTH: 25
<212> TYPE: DNA
<213> ORGANISM: Homo sapiens

<400> SEQUENCE: 8
gttatgggtt cccggttttt ttttt                                          25

<210> SEQ ID NO 9
<211> LENGTH: 21
<212> TYPE: DNA
<213> ORGANISM: Artificial Sequence
<220> FEATURE:
<223> OTHER INFORMATION: DPD forward primer

<400> SEQUENCE: 9
agtgagaaaa cggctgcata t                                              21

<210> SEQ ID NO 10
<211> LENGTH: 27
<212> TYPE: DNA
<213> ORGANISM: Artificial Sequence
<220> FEATURE:
<223> OTHER INFORMATION: DPD reverse primer

<400> SEQUENCE: 10
cattcaccaa cttatgccaa ttctctt                                        27
```

<210> SEQ ID NO 11
<211> LENGTH: 18
<212> TYPE: DNA
<213> ORGANISM: Artificial Sequence
<220> FEATURE:
<223> OTHER INFORMATION: HLA-B P1 forward primer

<400> SEQUENCE: 11
cgcgagtccg aggatggc                                                  18

<210> SEQ ID NO 12
<211> LENGTH: 24
<212> TYPE: DNA
<213> ORGANISM: Artificial Sequence
<220> FEATURE:
<223> OTHER INFORMATION: HLA-B P1 reverse primer

<400> SEQUENCE: 12
cgcagccata catcctctgg atga                                           24

<210> SEQ ID NO 13
<211> LENGTH: 19
<212> TYPE: DNA
<213> ORGANISM: Artificial Sequence
<220> FEATURE:
<223> OTHER INFORMATION: HLA-B P2 forward primer

<400> SEQUENCE: 13
ggagtattgg gaccggaac                                                 19

<210> SEQ ID NO 14
<211> LENGTH: 20
<212> TYPE: DNA
<213> ORGANISM: Artificial Sequence
<220> FEATURE:
<223> OTHER INFORMATION: HLA-B P2 reverese primer

<400> SEQUENCE: 14
gttgtagtag ccgcgcaggt                                                20

<210> SEQ ID NO 15
<211> LENGTH: 25
<212> TYPE: DNA
<213> ORGANISM: Artificial Sequence
<220> FEATURE:
<223> OTHER INFORMATION: CYP2C19 forward primer

<400> SEQUENCE: 15
tgcaataatt ttcccactat cattg                                          25

<210> SEQ ID NO 16
<211> LENGTH: 28
<212> TYPE: DNA
<213> ORGANISM: Artificial Sequence
<220> FEATURE:
<223> OTHER INFORMATION: CYP2C19 reverse primer

<400> SEQUENCE: 16
ctccaaaata tcactttcca taaaagca                                       28

<210> SEQ ID NO 17
<211> LENGTH: 23
<212> TYPE: DNA
<213> ORGANISM: Artificial Sequence
<220> FEATURE:

```
<223> OTHER INFORMATION: GAPDH-Forward primer

<400> SEQUENCE: 17
ggaaggtgaa ggtcggagtc ctc                                             23

<210> SEQ ID NO 18
<211> LENGTH: 24
<212> TYPE: DNA
<213> ORGANISM: Artificial Sequence
<220> FEATURE:
<223> OTHER INFORMATION: GAPDH-reverse primer

<400> SEQUENCE: 18
cctggaagat ggtgatggga tttc                                            24

<210> SEQ ID NO 19
<211> LENGTH: 101
<212> TYPE: DNA
<213> ORGANISM: Artificial Sequence
<220> FEATURE:
<223> OTHER INFORMATION: synthetic DNA sample
<220> FEATURE:
<221> NAME/KEY: misc_feature
<222> LOCATION: (51)..(51)
<223> OTHER INFORMATION: n is G or A.

<400> SEQUENCE: 19
catattggtg tcaaagtgtc actgaactaa aggctgactt tccagacaac ntaagtgtga     60
tttaacatct aaaacaagag aattggcata agttggtgaa t                        101

<210> SEQ ID NO 20
<211> LENGTH: 240
<212> TYPE: DNA
<213> ORGANISM: Artificial Sequence
<220> FEATURE:
<223> OTHER INFORMATION: Homo sapiens HLA-B allele B*15 as shown in
      Figure 7

<400> SEQUENCE: 20
gaggatggcg ccccgggcgc catggataga gcaggagggg ccggagtatt gggaccggaa     60
cacacagatc tccaagacca acacacagac ttaccgagag agcctgcgga acctgcgcgg   120
ctactacaac cagagcgagg ccgggtctca catcatccag aggatgtatg gctgcgacgt   180
ggggccggac gggcgcctcc tccgcgggta tgaccagtcc gcctacgacg gcaaggatta   240

<210> SEQ ID NO 21
<211> LENGTH: 18
<212> TYPE: DNA
<213> ORGANISM: Artificial Sequence
<220> FEATURE:
<223> OTHER INFORMATION: Homo sapiens HLA-B allele B*07 as shown in
      Figure 7

<400> SEQUENCE: 21
agaaggagcg ggcccccca                                                  18

<210> SEQ ID NO 22
<211> LENGTH: 14
<212> TYPE: DNA
<213> ORGANISM: Artificial Sequence
<220> FEATURE:
<223> OTHER INFORMATION: Homo sapiens HLA-B allele B*13 as shown in
      Figure 7

<400> SEQUENCE: 22
```
ggaccgctcc cata                                                    14

<210> SEQ ID NO 23
<211> LENGTH: 27
<212> TYPE: DNA
<213> ORGANISM: Artificial Sequence
<220> FEATURE:
<223> OTHER INFORMATION: Homo sapiens HLA-B allele B*27 as shown in
     Figure 7

<400> SEQUENCE: 23 agaaggggggg ggaccgctcc catccga                                     27

<210> SEQ ID NO 24
<211> LENGTH: 19
<212> TYPE: DNA
<213> ORGANISM: Artificial Sequence
<220> FEATURE:
<223> OTHER INFORMATION: Homo sapiens HLA-B allele B*38 as shown in
     Figure 7

<400> SEQUENCE: 24
agaagggatg ctcccccat                                               19

<210> SEQ ID NO 25
<211> LENGTH: 15
<212> TYPE: DNA
<213> ORGANISM: Artificial Sequence
<220> FEATURE:
<223> OTHER INFORMATION: Homo sapiens HLA-B allele B*39 as shown in
     Figure 7

<400> SEQUENCE: 25
agaaggaggc cccat                                                   15

<210> SEQ ID NO 26
<211> LENGTH: 11
<212> TYPE: DNA
<213> ORGANISM: Artificial Sequence
<220> FEATURE:
<223> OTHER INFORMATION: Homo sapiens HLA-B allele B*40 as shown in
     Figure 7

<400> SEQUENCE: 26
aagggcccca a                                                       11

<210> SEQ ID NO 27
<211> LENGTH: 16
<212> TYPE: DNA
<213> ORGANISM: Artificial Sequence
<220> FEATURE:
<223> OTHER INFORMATION: Homo sapiens HLA-B allele B*44 as shown in
     Figure 7

<400> SEQUENCE: 27
aaggggaccg ctccga                                                  16

<210> SEQ ID NO 28
<211> LENGTH: 15
<212> TYPE: DNA
<213> ORGANISM: Artificial Sequence
<220> FEATURE:
<223> OTHER INFORMATION: Homo sapiens HLA-B allele B*45 as shown in
     Figure 7

<400> SEQUENCE: 28
aagggcttgg ccata                                                   15

<210> SEQ ID NO 29
<211> LENGTH: 16
<212> TYPE: DNA
<213> ORGANISM: Artificial Sequence
<220> FEATURE:
<223> OTHER INFORMATION: Homo sapiens HLA-B allele B*46 as shown in
      Figure 7

<400> SEQUENCE: 29
ggagacgcgg gtcccc                                                    16

<210> SEQ ID NO 30
<211> LENGTH: 15
<212> TYPE: DNA
<213> ORGANISM: Artificial Sequence
<220> FEATURE:
<223> OTHER INFORMATION: Homo sapiens HLA-B allele B*48 as shown in
      Figure 7

<400> SEQUENCE: 30
agaaggggcc cccaa                                                     15

<210> SEQ ID NO 31
<211> LENGTH: 15
<212> TYPE: DNA
<213> ORGANISM: Artificial Sequence
<220> FEATURE:
<223> OTHER INFORMATION: Homo sapiens HLA-B allele B*50 as shown in
      Figure 7

<400> SEQUENCE: 31
aagggcttgg ccata                                                     15

<210> SEQ ID NO 32
<211> LENGTH: 19
<212> TYPE: DNA
<213> ORGANISM: Artificial Sequence
<220> FEATURE:
<223> OTHER INFORMATION: Homo sapiens HLA-B allele B*51 as shown in
      Figure 7

<400> SEQUENCE: 32
catatgctcc ttggccaaa                                                 19

<210> SEQ ID NO 33
<211> LENGTH: 20
<212> TYPE: DNA
<213> ORGANISM: Artificial Sequence
<220> FEATURE:
<223> OTHER INFORMATION: Homo sapiens HLA-B allele B*52 as shown in
      Figure 7

<400> SEQUENCE: 33
caggatgctc cttggccaaa                                                20

<210> SEQ ID NO 34
<211> LENGTH: 25
<212> TYPE: DNA
<213> ORGANISM: Artificial Sequence
<220> FEATURE:
<223> OTHER INFORMATION: Homo sapiens HLA-B allele B*54 as shown in
      Figure 7

<400> SEQUENCE: 34
aggaggggag cgggcttggc ccata                                          25

<210> SEQ ID NO 35
<211> LENGTH: 23
<212> TYPE: DNA
<213> ORGANISM: Artificial Sequence
<220> FEATURE:
<223> OTHER INFORMATION: Homo sapiens HLA-B allele B*55 as shown in
      Figure 7

<400> SEQUENCE: 35
agaaggagcg ggcttggccc ata                                          23

<210> SEQ ID NO 36
<211> LENGTH: 23
<212> TYPE: DNA
<213> ORGANISM: Artificial Sequence
<220> FEATURE:
<223> OTHER INFORMATION: Homo sapiens HLA-B allele B*56 as shown in
      Figure 7

<400> SEQUENCE: 36
agaaggagcg ggcttggccc ata                                          23

<210> SEQ ID NO 37
<211> LENGTH: 22
<212> TYPE: DNA
<213> ORGANISM: Artificial Sequence
<220> FEATURE:
<223> OTHER INFORMATION: Homo sapiens HLA-B allele B*57 as shown in
      Figure 7

<400> SEQUENCE: 37
ggggaatggt cggatgctcg tc                                           22

<210> SEQ ID NO 38
<211> LENGTH: 24
<212> TYPE: DNA
<213> ORGANISM: Artificial Sequence
<220> FEATURE:
<223> OTHER INFORMATION: Homo sapiens HLA-B allele B*58 as shown in
      Figure 7

<400> SEQUENCE: 38 cagggggaatg gtcggatgct cccc                                         24

<210> SEQ ID NO 39
<211> LENGTH: 23
<212> TYPE: DNA
<213> ORGANISM: Artificial Sequence
<220> FEATURE:
<223> OTHER INFORMATION: Homo sapiens HLA-B allele B*59 as shown in
      Figure 7

<400> SEQUENCE: 39
agaaggtatg ctccttggcc caa                                          23

<210> SEQ ID NO 40
<211> LENGTH: 18
<212> TYPE: DNA
<213> ORGANISM: Artificial Sequence
<220> FEATURE:
<223> OTHER INFORMATION: Homo sapiens HLA-B allele B*67 as shown in
      Figure 7

<400> SEQUENCE: 40
agaaggagcg ggccccat                                                18

```
<210> SEQ ID NO 41
<211> LENGTH: 10
<212> TYPE: DNA
<213> ORGANISM: Artificial Sequence
<220> FEATURE:
<223> OTHER INFORMATION: Homo sapiens HLA-B allele B*78 as shown in
      Figure 7

<400> SEQUENCE: 41
cttggccaaa                                                              10

<210> SEQ ID NO 42
<211> LENGTH: 10
<212> TYPE: DNA
<213> ORGANISM: Homo sapiens

<400> SEQUENCE: 42
acctgcgcgg                                                              10

<210> SEQ ID NO 43
<211> LENGTH: 14
<212> TYPE: DNA
<213> ORGANISM: Homo sapiens

<400> SEQUENCE: 43
catcatccag agga                                                         14

<210> SEQ ID NO 44
<211> LENGTH: 55
<212> TYPE: DNA
<213> ORGANISM: Artificial Sequence
<220> FEATURE:
<223> OTHER INFORMATION: synthetic DNA

<400> SEQUENCE: 44
aggaggggcc ggagtattgg gaccggaaca cacagatctc caagaccaac acaca            55

<210> SEQ ID NO 45
<211> LENGTH: 55
<212> TYPE: DNA
<213> ORGANISM: Artificial Sequence
<220> FEATURE:
<223> OTHER INFORMATION: synthetic DNA

<400> SEQUENCE: 45
aggaggggcc ggagtattgg gaccgggaga cacagatctc caagaccaac acaca            55

<210> SEQ ID NO 46
<211> LENGTH: 48
<212> TYPE: DNA
<213> ORGANISM: Artificial Sequence
<220> FEATURE:
<223> OTHER INFORMATION: synthetic DNA

<400> SEQUENCE: 46
ggccggagta ttgggaccgg aacacacaga tctccaagac caacacac                    48

<210> SEQ ID NO 47
<211> LENGTH: 48
<212> TYPE: DNA
<213> ORGANISM: Artificial Sequence
<220> FEATURE:
<223> OTHER INFORMATION: synthetic DNA

<400> SEQUENCE: 47
ggccggagta ttgggaccgg aacacacaga tctgcaagac caacacac                    48
```

<210> SEQ ID NO 48
<211> LENGTH: 48
<212> TYPE: DNA
<213> ORGANISM: Artificial Sequence
<220> FEATURE:
<223> OTHER INFORMATION: synthetic DNA

<400> SEQUENCE: 48
ggccggagta ttgggaccgg aacacacaga tcttcaagac caacacac        48

<210> SEQ ID NO 49
<211> LENGTH: 48
<212> TYPE: DNA
<213> ORGANISM: Artificial Sequence
<220> FEATURE:
<223> OTHER INFORMATION: synthetic DNA

<400> SEQUENCE: 49
ggccggagta ttgggaccgg aacacacaga tctacaagac caacacac        48

<210> SEQ ID NO 50
<211> LENGTH: 40
<212> TYPE: DNA
<213> ORGANISM: Artificial Sequence
<220> FEATURE:
<223> OTHER INFORMATION: synthetic DNA

<400> SEQUENCE: 50
agacttaccg agagagcctg cggaacctgc gcggctacta              40

<210> SEQ ID NO 51
<211> LENGTH: 40
<212> TYPE: DNA
<213> ORGANISM: Artificial Sequence
<220> FEATURE:
<223> OTHER INFORMATION: synthetic DNA

<400> SEQUENCE: 51
agacttaccg agagagcctg cggaccctgc tccgctacta              40

<210> SEQ ID NO 52
<211> LENGTH: 81
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (41)..(41)
<223> OTHER INFORMATION: n is G or A.

<400> SEQUENCE: 52
agatatgcaa taattttccc actatcattg attatttccc nggaacccat aacaaattac    60
ttaaaaacct tgcttttatg g                                               81